United States Patent
Wu et al.

(10) Patent No.: US 7,260,430 B2
(45) Date of Patent: Aug. 21, 2007

(54) ARCHITECTURE OF AN EMBEDDED INTERNET ROBOT SYSTEM CONTROLLED BY BRAIN WAVES

(75) Inventors: Li-Wei Wu, Taipei (TW); Hsien-Cheng Liao, Taipei (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 11/296,217

(22) Filed: Dec. 8, 2005

(65) Prior Publication Data

US 2006/0129277 A1    Jun. 15, 2006

(30) Foreign Application Priority Data

Dec. 10, 2004   (TW) ............................... 93138348 A

(51) Int. Cl.
*A61B 5/04* (2006.01)
(52) U.S. Cl. ...................... 600/545; 600/544
(58) Field of Classification Search ................ 600/544, 600/545, 300, 301; 128/920–925
See application file for complete search history.

(56) References Cited

U.S. PATENT DOCUMENTS

| | | | | |
|---|---|---|---|---|
| 5,363,858 A | * | 11/1994 | Farwell | 600/544 |
| 5,467,777 A | * | 11/1995 | Farwell | 600/544 |
| 5,974,262 A | * | 10/1999 | Fuller et al. | 710/8 |
| 6,001,065 A | * | 12/1999 | DeVito | 600/544 |
| 6,349,231 B1 | * | 2/2002 | Musha | 600/544 |
| 7,120,486 B2 | * | 10/2006 | Leuthardt et al. | 600/545 |
| 2005/0267597 A1 | * | 12/2005 | Flaherty et al. | 623/24 |

* cited by examiner

*Primary Examiner*—Navin Natnithithadha
(74) *Attorney, Agent, or Firm*—Rosenberg, Klein & Lee

(57) ABSTRACT

The present invention discloses an architecture of an embedded internet robot system controlled by brain waves, wherein the brain-computer interface and the internet robot system cooperate with the alertness level detection technology and the instruction translation technology, and thereby, the user can control a distal-end robot purely via consciousness activities and can interact with the environment as if there were an entity representing the user's consciousness appearing in the distal end. The seriously disabled person can regain his expressive ability via the present invention. Further, the present invention can also be applied to a multi-player interactive game system.

10 Claims, 1 Drawing Sheet

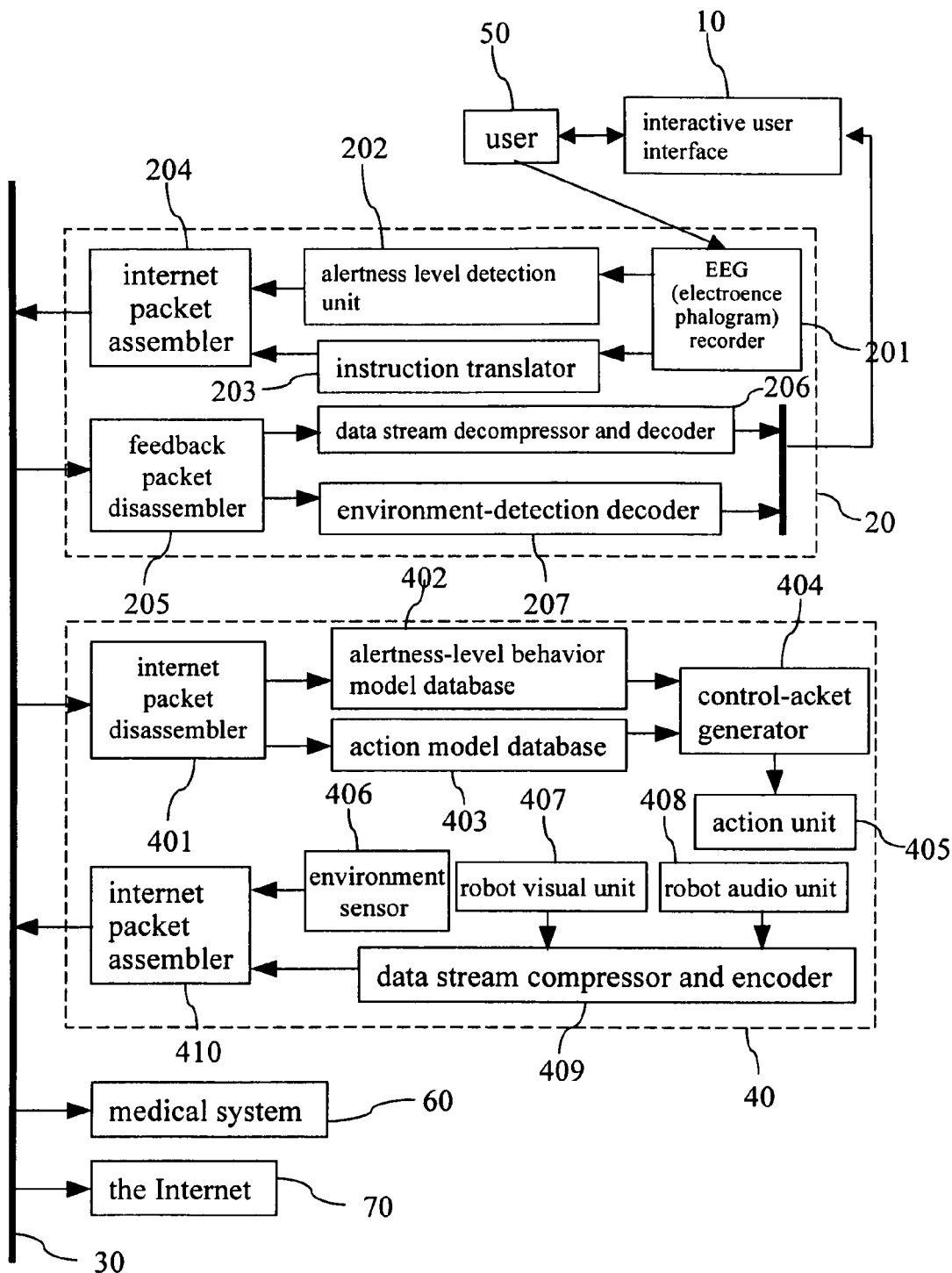

ARCHITECTURE OF AN EMBEDDED INTERNET ROBOT SYSTEM CONTROLLED BY BRAIN WAVES

BACKGROUND OF THE INVENTION

1. Field of the Invention

The present invention relates to an architecture of an embedded internet robot system, particularly to an architecture of an embedded internet robot system controlled by brain waves.

2. Description of the Related Art

BCI (Brain-Computer Interface) is a technology translating brain waves into instructions. The instructions translated from the brain waves can be used to control a computer and its peripheral devices, such a wheelchair. In many current researches, BCI is looked on as a control-instruction generator used to help the limb-disabled person generate instructions to control an artificial limb, a wheelchair, a computer, etc. However, so far, BCI can only be used in an undisturbed laboratory, and no BCI is used to control a distal-end system yet. Therefore, the application thereof is still limited.

As to the robot researches, the current control method of a robot still needs conventional input interfaces, such as a joystick, a keyboard, etc., and the top target of "act as you think" has not been achieved yet. At present, the studies on the robot performed by the academics focus on the applications in industrial control, family entertainment. As to the application in medicine, a medical robot usually plays the role of a nursing assistant.

Reviewing the current researches on brain science and robotics, we can find the applications thereof have the following drawbacks or bottlenecks:
1. The conventional BCI can only be used in an undisturbed laboratory and cannot provide movement freedom and medical care for the seriously disabled person.
2. The conventional BCI can only analyze action instructions and cannot detect the alertness level of the user.
3. The concept of reproducing one's consciousness in a distal end has not appeared yet in the current robotics and the conventional disabled equipments.
4. In the current consumer electronics, the 3G system has been matured, and T-backbone networks are extensively available, and various high efficiency protocols, such as IEEE 802.11 a/b/g, Bluetooth, UWB (Ultra Wideband), etc., have been proposed. However, the technology of the disabled equipments still lacks important progresses or breakthroughs because the market thereof is not so large, and even though the current disabled equipments are not so sophisticated, the price thereof is so high—the advanced science and technology does not take care of the disabled groups.

Accordingly, the present invention proposes an architecture of an embedded internet robot system controlled by brain waves, which combines BCI technology and robotics, in order to solve the abovementioned problems.

SUMMARY OF THE INVENTION

The primary objective of the present invention is to provide an architecture of an embedded internet robot system controlled by brain waves, which uses a brain-wave detection technology to enable the user to control a distal-end robot purely via a consciousness activity and interact with the environment as if there were an entity representing the user's consciousness appearing in a distal end.

Another objective of the present invention is to provide an architecture of an embedded internet robot system controlled by brain waves, whereby in addition to only receiving medical care, the seriously disabled person, who still has normal consciousness, normal visual and other sensory abilities, can also regain his expressive ability, move freely and interact with the society. Thus, the present invention can solve the problem that the conventional BCI is limited by the environment and cannot provide the disabled person with the freedom of movement.

Further objective of the present invention is to provide an architecture of an embedded internet robot system controlled by brain waves, wherein an alertness level detection technology enables the robot to have the alertness level of the user. Thereby, the present invention provides a better bi-directional intercourse and solves the problem that the conventional BCI cannot express the alertness level of the user.

Further another objective of the present invention is to provide an architecture of an embedded internet robot system controlled by brain waves, which can be applied to a multi-player interactive game system to promote the vividness of the game and can also be used to create new kinds of games.

To achieve the abovementioned objectives, the present invention proposes an architecture of an embedded internet robot system controlled by brain waves, which comprises: an interactive brain-computer interface (BCI), wherein the BCI is coupled to the user; a brain-computer interface system, wherein an electroencephalogram recorder measures and records the user's brain waves; an instruction translator converts the brain waves into at least one control instruction; an alertness level detection unit monitors the alertness level of the user via the brain waves and sends out at least one alertness-related instruction; and an internet packet assembler transmits those instructions to a network; and an embedded internet robot system, wherein an internet packet disassembler receives the packets of the control instructions and the alertness-related instructions from the network and then disassembles those packets; corresponding robot instructions are acquired from a built-in alertness-level behavior model database and a built-in action model database, and a control-packet generator creates action instructions to control an action unit to execute corresponding actions.

The embedded internet robot system of the present invention can have sensors for instantly acquiring visual, audio and other sensory information, and it will be fed back to the user of the BCI so that the user can interact with the environment.

The embodiments of the present invention are to be described below in detail in cooperation with the attached drawings in order to enable the objectives, technical contents, characteristics and accomplishments of the present invention to be more easily understood.

BRIEF DESCRIPTION OF THE DRAWINGS

The FIGURE is a schematic diagram of the architecture according to one embodiment of the present invention.

DETAILED DESCRIPTION OF THE INVENTION

The present invention proposes an architecture of an embedded internet robot system, which is based on a BCI (Brain-Computer Interface) technology and an architecture of an internet robot system, to cooperate with an alertness level detection technology of brain waves in order to enable the user to control a distal-end robot purely via consciousness activities and to interact with the environment.

Refer to the FIGURE, a schematic diagram of the architecture according to one embodiment of the present invention. The architecture of an embedded internet robot system controlled by brain waves disclosed in the present invention comprises: an interactive user interface 10; a brain-computer interface system 20; and an embedded internet robot system 40, connected to the brain-computer interface system 20 via a network 30. The network 30 may be an embedded Ethernet (IEEE 802.3), or an embedded wireless LAN (IEEE 802.11 a/b/g), or a Bluetooth network, or a UWB (Ultra Wideband) network. The brain-computer system 20 comprises: an EEG (electroencephalogram) recorder 201, an alertness level detection unit 202, an instruction translator 203, an internet packet assembler 204, a feedback packet disassembler 205, a data stream decompressor and decoder 206, an environment-detection decoder 207. The mobile embedded internet robot system 40 comprises: an internet packet disassembler 401, an alertness-level behavior model database 402, an action model database 403, a control-packet generator 404, an action unit 405, environment sensors 406, a robot visual unit 407, a robot audio unit 408, a data stream compressor and encoder 409, and an internet packet assembler 410.

Refer to the FIGURE again. The EEG recorder 201 records the user 50's EEG. The instruction translator 203 receives the EEG signals and translates them into instructions for the robot. The alertness level detection unit 202 detects and monitors the alertness level of the user 50. The outputs of the alertness level detection unit 202 and the instruction translator 203 are processed by the internet packet assembler 204 and transmitted to the embedded internet robot system 40 via the network 30. The embedded internet robot system 40 uses the internet packet disassembler 401 to disassemble the internet packets of the alertness level and the brain-wave instructions. From the built-in alertness-level behavior model database 402 and action model database 403, the embedded internet robot system 40 acquires corresponding robot actions according to different alertness levels and brain-wave instructions. The control-packet generator 404 creates robot action instructions to control the action unit 405, which includes: the mechanisms of the robot, motor systems, and brake systems, so that the internet robot system 40 can execute suitable actions and behave appropriately.

The robot visual unit 407 and robot audio unit 408 can detect images and sounds around the environment of the robot. The detected images and sounds are compressed and encoded by the data stream compressor and encoder 409 and processed by the internet packet assembler 410 and then fed back to the brain-computer interface system 20 via the network 30. The feedback packet disassembler 205 disassembles the packets, and the disassembled packets are decompressed and decoded by the data stream decompressor and decoder 206 into video and audio information, which is further fed back to the interactive user interface 10 and sensed by the user 50. The environment sensors 406 can detect the external environment factors, such as temperature, pressure, gas concentration, invaders, etc. The detection signals of the environment sensor 406 are processed by the internet packet assembler 410 and then sent to the brain-computer interface system 20 via the network 30. The packets are also disassembled by the feedback packet disassembler 205 and then decoded by the environment-detection decoder 207. The decoded information is fed back to the interactive user interface 10, and thus, the user 50 can monitor the external surroundings.

The abovementioned interactive user interface 10 not only can simultaneously and instantly display the alertness level of the user 50 and the control command made by the user 50 but also can instantly present distal-end images and sounds to the user 50. Thereby, the user 50 has a user-friendly environment to sense the surroundings of the internet robot system 40.

The alertness level detection algorithm is used in the alertness level detection unit 202. The brain waves can be classified into a slow wave ($\theta$ and $\delta$ waves), an $\alpha$ wave and a $\beta$ wave. When a normal person is relaxed, a mass of $\alpha$ waves (7~14 Hz) appears in the EEG. When he is alert, $\beta$ waves (14~20 Hz) dominate the EEG. When he falls into deep sleep, $\theta$ waves (3.5~7 Hz) and $\delta$ waves (1~3.5 Hz) appear. Based on those characteristics, the present invention uses a second order AR model (auto-regression model) of subband components to undertake the alertness level detection. The present invention can work out which level of alertness the user is in, i.e. which one of the alert, relaxed and sleeping states the user is in. The worked out alertness level is then sent to the distal-end embedded internet robot system 40 and processed therein to output corresponding robot actions.

Refer to the FIGURE again. The instruction translator 203 is used to identify the characteristics of the user's brain waves and issue corresponding instructions. When the user moves his limbs, the mu rhythm of 7~10 Hz and the beta rhythm of 15~30 Hz measured in the motor area will decay. In the BCI of the present invention, the EEG will be sent to a band-pass filter (not shown in the drawings), and the band powers of the mu rhythm and the beta rhythm are selected to be feature vectors. The selected feature vectors are used to train a Fisher discriminant, and a brain-wave discriminant is thus obtained. The BCI uses the band powers and the linear discriminant analysis to identify the characteristics of the brain waves and then issues instructions to the computer.

The embedded internet robot system of the present invention can integrate with a prior art of Taiwan Patent application No. 93109415 and have the advantages of low cost, high transmission rate, high fault tolerance, high system integration capability, high energy efficiency, and high reproducibility. The present invention can easily connect with a cluster system, a medical system 60 and the Internet 70 showing in FIGURE.

In summary, in the present invention, the brain waves created by the user's consciousness are transformed into instructions and alertness levels, which is transmitted via a network, to control a physical robot and express his thinking, and the images and sounds sensed the robot can be fed back to the user so that he can interact with the environment. The present invention allows others to acquire the user's alertness level and amend or install software of the robot system. In the present invention, the message transmission can be undertaken via the linkage with a personal computer, or an internet household appliance, etc. When the detected alertness level or physiological status of the user is abnormal, the robot system will inform the emergency medical system. The relatives or friends of the user can also acquire the instant information of the user from the robot system via the Internet in order to understand the latest condition of the user. Further, the present invention can also be applied to a multi-player interactive game, and the brain-wave control can cooperate with the conventional joystick control to create new kinds of games.

Herein, the characteristics and efficacies of the present invention are to be further stated below:

1. superior capability of controlling complicated mechanisms and renewing the action model database: in contrast with the conventional brain-wave control system wherein the response speed is low, and the brain-wave modes it can recognize do not provide abundant and sophisticated instructions but can only control few low-freedom actions, and it is hard to control a platform or system of high response speed and high movement freedom, the robot architecture of the present invention not only can instantly control high-freedom actions but also can learn and add new action models to the action model database for providing the user with more action options;
2. ability to express the alertness level of the user: the alertness level can be extracted by an appropriate discriminant and then expressed by the limb movements, images, virtual emotional expressions, or virtual reality of the robot; the internet robot system can start, close, or shift corresponding functions according to the detected alertness level;
3. converting brain waves into control instructions: with the BCI technology, the present invention can convert brain waves into control instructions and perform complicated control operations or interactions according to the action model database;
4. promoting expressive ability: Via the present invention, the seriously disabled person can regain the ability to express his feeling; the seriously person's feeling can be clearly expressed with the system of the present invention and presented to his family members in a distal end; thus, he can have a better intercourse with his family, and the living quality of him and his family can also be promoted;
5. promoting self-care ability: The present invention can help the seriously disabled person take care of himself; the action model database, which can learn, can be taught various complicated functions so that the patient or the user can take care of himself via the instructions of the BCI;
6. creating employment opportunities: The present invention can help the seriously disabled person regain employment and relax the burden of his family and the society; the appearance and the contents of the action model database of the robot can be designed according to the needs of various occupations, which may give the seriously disabled person employment opportunities; for example, the distal-end reproduction of the images and sounds sensed by the robot can be used in the watch, patrol or emergency informing of a security job; the embedded internet robot system controlled by brain waves can also be used to communicate with others by the disabled persons of some professions, such as writers, dramatists, painters, or even by a president, who is unable to declare his will in voice;
7. superior capability of exchanging information and obtaining extensive prevalence: the present invention is based on TCP/IP (Transmission Control Protocol/Internet Protocol) and has many options in wired networks; IEEE 802.11 a/b/g further provides a high speed and low cost environment for a wireless network;
8. economic communication and expansion interfaces: the present invention is based on TCP/UDP (User Datagram Protocol)/IP protocol; owing to the prevalence of personal computes and the Internet, the cost of MAC (multimedia access controller) is lowered now; thus, the cost of communication and expansion is also reduced, and the present invention can conveniently integrate with a mobile phone or a PDA;
9. superior applicability in a general family: on the contrary, the conventional BCI can only be used in a laboratory or a hospital;
10. providing bidirectional video and audio communication: the user can receive the images and sounds fed back by video and audio sensors and interact with others; the family of the seriously disabled person can send an instant message to him from a distal end via the robot's visual and audio sensors without driving a long way to communicate face to face;
11. superior capability of linking together the medical-care system and the user's family: as the present invention uses the current protocol, the personnel of the medical center can easily monitor the physiological status of the user instantly and anytime; also, the present invention can instantly detect any emergency and inform the medical-care system to offer a first aid promptly;
12. superior portability: based on TCP/UDP/IP protocol, the present invention further cooperates with embedded Ethernet/wireless network technology and the prior art of Taiwan Patent application No. 93109415 in order to lower the cost, raise the efficiency, reduce the size and save the power; thus, the portability of the system is promoted; in cooperation with a wireless network, the present invention can have a further better operability; the present invention can also integrate with general commercial electronic products, such as electronic game machines;
13. task-oriented appearance and functions: the protocol of the present invention is implemented with TCP/UDP/IP packets, and TCP/UDP/IP are common and standard protocols; thus, the control-related packets, which has a person's consciousness, can be rapidly implanted into another robot having different appearance and functions in order to meet different demands or execute different tasks;
14. avoiding directly confronting a danger: via the present invention, the disabled person can extend his visual and hearing field without moving everywhere by himself but just by controlling the robot to see and hear with the brain waves of his thinking; the robot of the present invention can also be used to handle a dangerous case, and once harm really happens, it is not the user but the robot that is hurt.

Those embodiments disclosed above are only to clarify the present invention to enable the persons skilled in the art to understand, make and use the present invention; however, those are not intended to limit the scope of the present invention. Any equivalent modification and variation according to the spirit of the present invention disclosed herein is to be included within the scope of the present invention.

What is claimed is:

1. An architecture of an embedded internet robot system controlled by brain waves, comprising:
   at least one interactive user interface, coupled to the user
   a brain-computer interface system for determining a physical action cognitively intended by the user, said brain-computer interface system comprising: an electroencephalogram recorder to measure and record the user's brain waves; an instruction translator, converting said brain waves into at least one brain-wave instruction; an alertness level detection unit, monitoring the alertness level of the user via said brain waves and sending out at least one alertness related instruction; and an internet packet assembler, assembling said instructions sent from said instruction translator and said alertness level detection unit into packets and then sending said packets to a network;

an embedded internet robot system remotely disposed from said interactive user interface for responsively replicating the cognitively intended physical action, said embedded internet robot system comprising: an internet packet disassembler receiving and disassembling said packets of said instructions of said instruction translator and said alertness level detection unit from said network; built-in alertness-level behavior model and action model databases for storing alertness-related and action related model information for acquiring corresponding robot instructions according to said model information; an action unit to execute actions; a control-packet generator creating action instructions to control said action unit to undertake corresponding actions; and, at least one environment sensor detecting an environmental factor about the embedded internet robot system for interactive feedback to the user.

2. The architecture of an embedded internet robot system controlled by brain waves according to claim 1, wherein said internet robot system further comprises: a robot visual unit for detecting images and a robot audio unit for detecting sounds; the detected images and sounds are compressed and encoded by a data stream compressor and encoder and then processed by a internet packet assembler into packets, and then said packets are fed back to said brain-computer interface system via said network; said brain-computer interface system further comprises: a feedback packet disassembler and a data stream decompressor and decoder; said packets of images and sounds are disassembled by said feedback packet disassembler and then decompressed and decoded by said data stream decompressor and decoder and then fed back to said interactive user interface.

3. The architecture of an embedded internet robot system controlled by brain waves according to claim 1, wherein said internet robot system further comprises: a plurality of said environment sensors operable to detect the external environment factors; the detection signals of said environment sensor are processed by an internet packet assembler into packets, and then said packets are fed back to said brain-computer interface system via said network; said brain-computer interface system further comprises: a feedback packet disassembler and an environment-detection decoder; said packets are disassembled by said feedback packet disassembler and then decoded by said environment-detection decoder and then fed back to said interactive user interface of the user.

4. The architecture of an embedded internet robot system controlled by brain waves according to claim 3, wherein said external environment factors are selected from the group consisting of: temperature, pressure, gas concentration and invader.

5. The architecture of an embedded internet robot system controlled by brain waves according to claim 1, wherein the alertness level detection algorithm is used in said alertness level detection unit; based on the characteristics of the brain waves, the states of the user are classified into a relaxed state, a alert state, and a sleeping state.

6. The architecture of an embedded internet robot system controlled by brain waves according to claim 5, wherein when the user is in said relaxed state, a mass of $\alpha$ waves (7~14 Hz) appears in his brain waves; when the user is in said alert state, $\beta$ waves (14~20 Hz) dominate his brain waves; when the user is in said sleeping state, $\theta$ waves (3.5~7 Hz) and $\delta$ waves (1~3.5 Hz) appear in his brain waves; according to the abovementioned characteristics of brain waves, brain waves are classified into a slow wave ($\theta$ and $\delta$ waves), an $\alpha$ wave and a $\beta$ wave.

7. The architecture of an embedded internet robot system controlled by brain waves according to claim 1, wherein said action unit further comprises: mechanisms of the robot, a motor system and a brake system.

8. The architecture of an embedded internet robot system controlled by brain waves according to claim 1, wherein said brain-computer interface system or said internet robot system can link a medical system via said network.

9. The architecture of an embedded internet robot system controlled by brain waves according to claim 1, wherein said brain-computer interface system or said internet robot system can further link an internet via said network.

10. The architecture of an embedded internet robot system controlled by brain waves according to claim 1, wherein said network, which transmits signal packets, is selected from the group of embedded Ethernet (IEEE 802.3), embedded wireless LAN/Wi-Fi (Wireless Fidelity)(IEEE 802.11 a/b/g), Bluetooth network, and UWB (Ultra Wideband) network.

* * * * *